(12) United States Patent
Yoneda et al.

(10) Patent No.: US 7,807,840 B2
(45) Date of Patent: Oct. 5, 2010

(54) PROCESS FOR PREPARING OPTICALLY ACTIVE AMINOPENTANE DERIVATIVE, INTERMEDIATE AND PROCESS FOR PREPARING INTERMEDIATE

(75) Inventors: Fumio Yoneda, Matsubara (JP); Mayumi Watanabe, Matsubara (JP); Takuya Yasusa, Matsubara (JP)

(73) Assignee: Fujimoto Co., Ltd., Osaka (JP)

( * ) Notice: Subject to any disclaimer, the term of this patent is extended or adjusted under 35 U.S.C. 154(b) by 170 days.

(21) Appl. No.: 11/922,925

(22) PCT Filed: Jun. 28, 2006

(86) PCT No.: PCT/JP2006/312869

§ 371 (c)(1),
(2), (4) Date: Dec. 27, 2007

(87) PCT Pub. No.: WO2007/001015

PCT Pub. Date: Jan. 4, 2007

(65) Prior Publication Data

US 2009/0124813 A1  May 14, 2009

(30) Foreign Application Priority Data

Jun. 28, 2005  (JP) .............................. 2005-187519

(51) Int. Cl.
*C07C 209/00* (2006.01)
*C07D 291/04* (2006.01)
(52) U.S. Cl. ...................................... 548/122; 564/413
(58) Field of Classification Search ................ 564/413; 548/122
See application file for complete search history.

(56) References Cited

FOREIGN PATENT DOCUMENTS

WO          01/77074          10/2001

OTHER PUBLICATIONS

M. K. Pound et al., "New Carbon-Carbon Bond Forming Reactions of Cyclic Sulfate Esters and Cyclic Sulfamidates", Tetrahedron Letters, vol. 43, pp. 1915-1918, 2002.

*Primary Examiner*—Kamal A Saeed
*Assistant Examiner*—Samantha L Shterengarts
(74) *Attorney, Agent, or Firm*—Wenderoth, Lind & Ponack, L.L.P.

(57) ABSTRACT

There are provided a process for preparing an optically active aminopentane derivative that is promising as a psychotropic agent, an antidepressant agent, an antiparkinsonian agent, an anti-Alzheimer's agent, an apoptosis inhibitor, or the like; a novel optically active intermediate oxathiazolidine derivative very useful in the production of the aminopentane derivative; and process for the production thereof.

The optically active aminopentane derivatives can be produced in an industrially advantageous manner from a novel optically active oxathiazolidine derivative represented by formula (5):

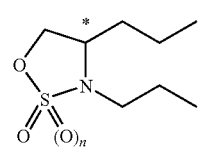

(5)

wherein * indicates the position of an asymmetric carbon atom in the R or S configuration, and n is 0 or 1.

4 Claims, No Drawings

PROCESS FOR PREPARING OPTICALLY ACTIVE AMINOPENTANE DERIVATIVE, INTERMEDIATE AND PROCESS FOR PREPARING INTERMEDIATE

This application is a U.S. national stage of International Application No. PCT/JP2006/312869 filed Jun. 28, 2006.

TECHNICAL FIELD

The invention relates to a process for preparing an optically active aminopentane derivative that is promising as a psychotropic agent, an antidepressant agent, an antiparkinsonian agent, an anti-Alzheimer's agent, an apoptosis inhibitor, or the like. The invention also relates to a novel intermediate for preparing the aminopentane derivative and a process for preparing the intermediate.

BACKGROUND ART

A particular class of aminopentane derivatives have already been described as having a catecholaminergic activity enhancing effect (CAE effect) by enhancing membrane potential dependent exocytosis, which effect differs from that of monoamine oxidase inhibitors, catecholamine uptake inhibitors or catecholamine substitution type release stimulating agents (for example, see Patent Literature 1 listed below). In particular they have been described to be devoid of excessive catecholamine release or amine depletion at catecholamine nerve terminals, which are observed with catecholamine substitution type release stimulating agents.

Such aminopentane derivatives are expected to have fewer side effects such as abnormal hyperactivity (excitatory effect) and neurotoxicity in the central nervous system, to have fewer problems such as decreasing responsiveness of patients, and to be highly effective as a safe and useful antidepressant, psychotropic, antiparkinsonian, or anti-Alzheimer's agents. It has also been reported that the aminopentane derivatives have an asymmetric carbon in the molecular structure and optically active isomers of them were found to be more effective than racemates (for example, see Patent Literature 2 and Non-Patent Literature 1 listed below).

Concerning 1-(benzofuran-2-yl)-2-propylaminopentane, for example, the (−) form with the R configuration has a higher pharmacological activity as compared with the (+) form with the S configuration or the racemate (see Patent Literature 2 and Non-Patent Literature 1). In addition, it is disclosed that the (R)-1-(benzofuran-2-yl)-2-propylaminopentane has an anti-apoptosis activity and is potentially useful as an apoptosis inhibitor against Alzheimer's disease, Parkinson's disease, Huntington's disease, amyotrophic lateral sclerosis, retinitis pigmentosa, glaucoma, nervous diseases such as spinocerebellar degeneration, ischemic brain diseases such as stroke, neurodegenerative diseases such as peripheral nerve disorder observed in diabetes, AIDS, and toxic diseases (for example, see Patent Literature 3 listed below).

Conventionally known process for preparing optically active aminopentane derivatives such as (R)-1-(benzofuran-2-yl)-2-propylaminopentane comprises a synthesis of the racemates from various aromatic aldehydes via nitroalkene intermediates followed by their optical resolution. However, such processes require not only an equivalent amount or more of a reagent, such as an optically active acid, to the amine but also troublesome operation such as crystallization, separation and purification. For example, optically active (R)-1-(benzofuran-2-yl)-2-propylaminopentane could not be obtained from a synthesized racemate by an optical resolution via formation of diastereomeric salts or derivatives but could only be separated by preparative high-performance liquid chromatography using a chiral column. Such separation requires a large amount of solvent and a lot of time and is a less productive method by which only at most about 50% of the desired optically active substance can be recovered (see Patent Literatures 1 and 2). Other methods using enzymes and some asymmetric synthesis methods are also known and they might be applicable to a preparation of the aminopentanes, however, these methods are less practical in view of limited substrates, insufficient selectivity and complicated operation.

Thus, there have been developed two different practical processes for preparing optically active 1-(benzofuran-2-yl)-2-propylaminopentane. The first process comprises treating an optically active aziridine derivative prepared from an optically active norvaline with 2-benzofuran lithium to build up a framework of the optically active 1-(benzofuran-2-yl)-2-propylaminopentane. The second process comprises treating an optically active N-methoxy-N-methylamide derivative prepared from an optically active norvaline with 2-benzofuran lithium to obtain a ketone and reducing the ketone to build up a framework of the optically active 1-(benzofuran-2-yl)-2-propylaminopentane. The development of these two processes allows efficient production of both optically active isomers of 1-(benzofuran-2-yl)-2-propylaminopentane (see Patent Literature 4 listed below). However, research and development has been carried out in order to seek more industrially advantageous processes than these processes.

Patent Literature 1: Pamphlet of International Publication No. WO99/07667
Patent Literature 2: Japanese Patent Application Laid-Open (JP-A) No. 2000-136187
Patent Literature 3: JP-A No. 2003-89643
Patent Literature 4: Pamphlet of International Publication No. WO01/77074
Non-Patent Literature 1: Yoneda et al., Bioorganic & Medicinal Chemistry, 2001 Vol. 9, pp. 1197-1212

DISCLOSURE OF THE INVENTION

Objects of the Invention

It is an object of the invention to provide a novel process for preparing an optically active aminopentane derivative useful as a psychotropic agent, an antidepressant agent, an antiparkinsonian agent, an anti-Alzheimer's agent, an apoptosis inhibitor, or the like, to provide a novel intermediate for preparing the optically active aminopentane derivative, and to provide a process for preparing the intermediate.

Means for Solving the Problems

As a result of intensive investigations, the inventors have found a novel optically active oxathiazolidine derivative represented by formula (5):

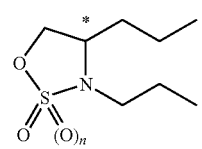

wherein * indicates the position of an asymmetric carbon atom in the R or S configuration, and n represents 0 or 1, is a very useful intermediate, which can be prepared from a commercially available optically active norvaline, in the production of the optically active aminopentane derivative.

The inventors have also found a novel process for preparing an optically active aminopentane derivative via the above novel intermediate.

Specifically, the inventors have found that the optically active propylaminopentane derivative represented by formula (8):

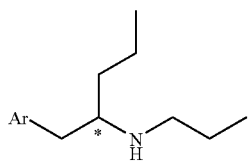
(8)

wherein Ar represents an aryl group and * indicates the position of an asymmetric carbon atom in the R or S configuration, can be easily prepared in high selectivity and good yield by the following steps:

treating an optically active oxathiazolidine derivative represented by formula (5-1):

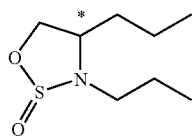
(5-1)

wherein * has the same meaning as defined above, with an oxidizing agent in the presence of a ruthenium catalyst to obtain an optically active oxathiazolidine derivative represented by formula (5-2):

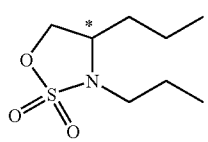
(5-2)

wherein * has the same meaning as defined above;

treating the oxathiazolidine derivative with an aryl lithium represented by formula (6):

Ar—Li    (6)

wherein Ar has the same meaning as defined above to obtain an optically active lithium N-sulfonate derivative represented by formula (7):

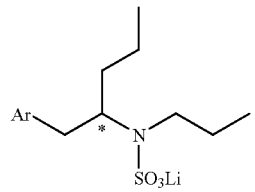
(7)

wherein Ar and * each has the same meaning as defined above; and hydrolyzing the above lithium N-sulfonate with an acid to obtain an optically active propylaminopentane derivative represented by formula (8):

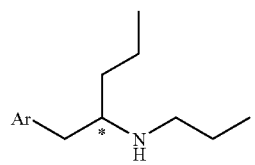
(8)

wherein Ar and * each has the same meaning as defined above. Thus, the invention has been completed.

The optically active oxathiazolidine derivative represented by formula (5) as a novel intermediates comprise the compounds represented by formulae (5-1) and (5-2), and can be prepared by the process described below.

i) Esterification of an optically active norvaline represented by formula (1):

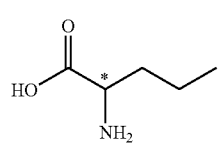
(1)

wherein * has the same meaning as defined above, with an alcohol pretreated with thionyl chloride to give an optically active norvaline ester derivative represented by formula (2):

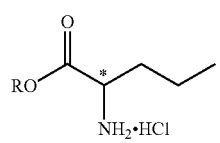
(2)

wherein R represents a lower alkyl group, and * has the same meaning as defined above. In this step, for example, the alcohol may be a lower $C_1$ to $C_6$ alcohol such as methanol, ethanol or propanol, preferably a lower $C_1$ to $C_3$ alcohol. This reaction may be performed under conventional conditions for esterification using thionyl chloride and alcohols.

ii) Amidation of the above ester derivative with propionic anhydride in the presence of a base and in a solvent to give an optically active N-propionylnorvaline ester derivative represented by formula (3):

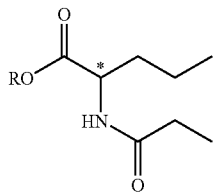

(3)

wherein R and * each has the same meaning as defined above. In this step, for example, the solvent may be water or a combination of water and an organic solvent such as dichloromethane or ethyl acetate. The base may be an inorganic base such as sodium hydrogen carbonate, sodium carbonate, potassium hydrogen carbonate, or potassium carbonate, or an organic base such as triethylamine, pyridine or N-methylmorpholine. The reaction temperature is generally from 0 to 40° C., preferably from 15 to 20° C., and the reaction time is generally from 30 minutes to 1 day, preferably from 1 to 3 hours.

iii) Reduction of the carboxyl group and the amide group in the above amide derivative with a reducing agent in a solvent to give an optically active N-propylnorvalinol represented by formula (4):

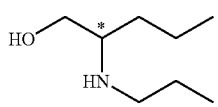

(4)

wherein * has the same meaning as defined above. In this step, for example, the reaction solvent may be an organic solvent such as tetrahydrofuran, diethyl ether, and diisopropyl ether. The reducing agent may be a known reducing agent such as lithium aluminum hydride. The reaction temperature is generally from 20 to 120° C., preferably from 35 to 70° C., and the reaction time is generally from 2 hours to 1 day, preferably from 2 to 4 hours.

iv) Formation of a 1,2,3-oxathiazolidine ring from the above propylnorvalinol using thionyl chloride in the presence of a base and in a solvent to give an optically active oxathiazolidine derivative represented by formula (5-1):

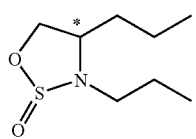

(5-1)

wherein * has the same meaning as defined above. In this step, for example, the solvent may be an organic solvent such as dichloromethane, 1,2-dichloroethane, ethyl acetate, toluene, acetonitrile, tetrahydrofuran, N,N-dimethylformamide, acetone, or hexane. For example, the base may be an organic base such as triethylamine, imidazole, N-methylmorpholine, pyridine, or N,N-diisopropylethylamine. The reaction temperature is generally from −20 to 60° C., preferably from −15 to 30° C., and the reaction time is generally from 30 minutes to 1 day, preferably from 3 to 4 hours.

v) Oxidation of the above oxathiazolidine derivative with an oxidizing agent in the presence of a ruthenium catalyst and in a solvent to give an optically active oxathiazolidine derivative represented by formula (5-2):

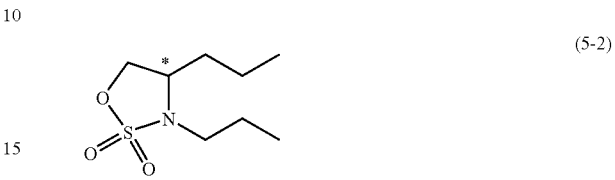

(5-2)

wherein * has the same meaning as defined above. In this step, for example, the solvent may be a mixture of water and an organic solvent such as ethyl acetate, acetonitrile, diisopropyl ether, dichloromethane, or 1,2-dichloroethane, or a mixture of a buffer solution such as a phosphate buffer solution and an organic solvent such as ethyl acetate, acetonitrile, diisopropyl ether, dichloromethane, or 1,2-dichloroethane. For example, the ruthenium catalyst may be ruthenium trichloride, ruthenium dioxide or the like. For example, the oxidizing agent may be sodium periodate, an aqueous sodium hypochlorite solution, or the like. The reaction temperature is generally from 0 to 40° C., and the reaction time is generally from about 1 to 3 hours. 3,4-Dipropyl-1,2,3-oxathiazolidine 2-oxide, which is an optically active oxathiazolidine derivative of formula (5-1), has additional chiral center at the sulfur atom and thus may be a mixture of diastereoisomers, in which the component ratio may depend on the reaction conditions in the above step iv). Regardless of the ratio of diastereoisomers, however, 3,4-dipropyl-1,2,3-oxathiazolidine 2,2-dioxide, which is an optically active oxathiazolidine derivative of formula (5-2), can be obtained in the step v). From the novel optically active oxathiazolidine derivative of formula (5) thus obtained, the desired optically active aminopentane derivative can be prepared by the process described below.

vi) Ring opening reaction of the above oxathiazolidine derivative of formula (5-2) with an aryl lithium represented by formula (6) in a solvent to give an optically active lithium N-sulfonate derivative represented by formula (7):

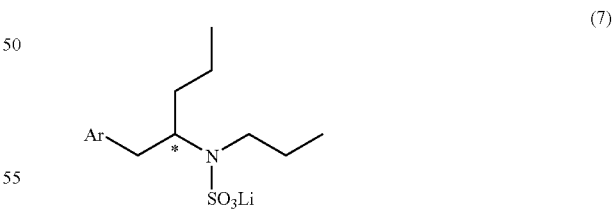

(7)

wherein Ar and * each has the same meaning as defined above. For example, the aryl group represented by Ar may be phenyl, thienyl, naphthyl, benzofuryl, benzothienyl, methylenedioxyphenyl, or indolyl. The aryl group may have a substituent(s) such as $C_1$ to $C_3$ alkyl on its aromatic ring, if it does not obstruct the reaction. The aryl lithium may be prepared by treating a corresponding aromatic compound with n-butyl lithium. The step vi) is be performed in an appropriate solvent. For example, such a solvent may be an organic solvent such as tetrahydrofuran or diethyl ether. In this step, if desired, an additive such as N,N,N',N'-tetramethylethylenediamine or 1,2-dimethoxyethane may be added as appropriate. The sulfonate derivative can be obtained as a reaction mixture or can be obtained as an aqueous solution by liquid-liquid separation after water is added to the reaction mixture. The reaction is preferably performed under an inert atmosphere (nitrogen or argon, preferably nitrogen). The reaction temperature is generally from −10 to 10° C., and the reaction time is generally from 1 to 4 hours.

vii) Hydrolysis of the above sulfonate derivative in the reaction mixture or in the aqueous solution thereof with an acid to give an optically active aminopentane derivative represented by formula (8):

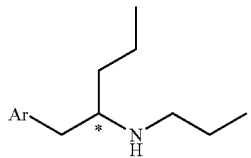

(8)

wherein Ar and * each has the same meaning as defined above. In this step, for example, the acid may be hydrochloric acid, sulfuric acid, hydrobromic acid, or the like. The reaction temperature is generally from 0 to 40° C., and the reaction time is generally from about 1 hour to about 1 day.

The resulting aminopentane derivative may be converted into a pharmacologically acceptable acid addition salt thereof, which includes an inorganic acid such as hydrochloric acid, sulfuric acid, hydrobromic acid, nitric acid, or methanesulfonic acid, or a salt of an organic acid such as gluconic acid, tartaric acid, maleic acid, fumaric acid, succinic acid, malic acid, citric acid, or mandelic acid.

There is no particular limitation on the reaction temperature and the reaction time in each step described above, however, they are preferably within the range of the conventional conditions in each step in view of the properties of the reaction reagents.

EFFECTS OF THE INVENTION

The use of the novel optically active oxathiazolidine derivative represented by formula (5) as a production intermediate facilitates the efficient production of both optically active aminopentane derivative isomers with high purity and establishes industrially advantageous process for preparing optically active aminopentane derivatives.

BEST MODE FOR CARRYING OUT THE INVENTION

The invention is described in more detail with reference to the following examples which are not intended to limit the scope of the invention.

EXAMPLES

Example 1

Synthesis of (R)-Norvaline Methyl Ester

Thionyl chloride (47.7 mL) was added dropwise to methanol (300 mL) under stirring at −5° C. over 2 hours and 15 minutes. D-Norvaline (35.00 g) was added to the resulting light yellow solution under stirring at −4° C. The solution was stirred at room temperature for 18 hours and then methanol was removed under reduced pressure. Disopropyl ether (90 mL) was added to the precipitated crystals, which were filtered and washed twice with diisopropyl ether (30 mL) to give (R)-norvaline methyl ester (47.74 g, 95% yield) as a white powder.

Melting point: 109-110° C.

MS (m/z) 132, 88, 72

IR (KBr) 3440, 2970, 1753, 1585, 1502, 1443, 1382, 1283, 1243, 1165, 1123, 1032, 994, 937, 898, 740 cm$^{-1}$

NMR (CDCl$_3$) δ 0.97 (t, 3H, J=7.4 Hz), 1.38-1.75 (m, 2H), 2.05 (q, 2H, J=7.4 Hz), 3.82 (s, 3H), 4.18 (t, 1H, J=6.4 Hz), 8.45-9.15 (br, 3H) ppm Specific rotation: $[\alpha]_D^{20}$−20.51° (CHCl$_3$, c=1.056)

Example 2

Synthesis of (S)-Norvaline Methyl Ester (S)—Norvaline methyl ester (18.2 g, 100% yield) was obtained as a colorless crystals, following the procedure of Example 1, but using L-norvaline (12.7 g) and thionyl chloride (17.3 mL).

Example 3

Synthesis of (R)—N-Propionylnorvaline Methyl Ester (R)—Norvaline methyl ester (30.35 g) was added to an aqueous solution (180 mL) of sodium hydrogen carbonate (15.21 g) under ice-cooling and stirring and then stirred for 5 minutes under ice-cooling. Propionic anhydride (25.5 mL) and sodium hydrogen carbonate (8.36 g) were slowly and alternately added to the resulting solution and stirred for 1 hour under ice-cooling. The resulting two-layer solution was extracted with ethyl acetate (90 mL). The organic layer was washed with a saturated aqueous sodium hydrogen carbonate solution (50 mL), dried over anhydrous sodium sulfate and then concentrated under reduced pressure to give (R)—N-propionylnorvaline methyl ester (33.79 g, 99% yield) as a pale yellow oil.

IR (KBr) 3295, 3060, 2955, 2870, 1742, 1651, 1540, 1460, 1440, 1378, 1206, 1157, 1068, 1020 cm$^{-1}$

NMR (CDCl$_3$) δ 0.93 (t, 3H, J=7.4 Hz), 1.17 (t, 3H, J=7.7 Hz), 1.23-1.48 (m, 2H), 1.56-1.72 (m, 1H), 1.74-1.89 (m, 1H), 2.26 (q, 2H, J=7.7 Hz), 3.74 (s, 3H), 4.63 (dt, 1H, J=5.4, 7.4 Hz), 5.87-6.20 (br, 1H) ppm Specific rotation: $[\alpha]_D^{20}$−20.91° (CHCl$_3$, c=1.006)

Example 4

Synthesis of (S)—N-Propionylnorvaline Methyl Ester (S)—N-Propionylnorvaline methyl ester (20.7 g, 100% yield) was obtained as a slightly yellowish oil, following the procedure of Example 3, but using (S)-norvaline methyl ester (18.2 g) and propionic anhydride (14.9 g). NMR (CDCl$_3$) δ 0.93 (t, 3H, J=7.4 Hz), 1.17 (t, 3H, J=7.4 Hz), 1.23-1.50 (m, 2H), 1.50-1.72 (m, 1H), 1.72-1.90 (m, 1H), 2.26 (q, 2H, J=7.4 Hz), 3.74 (s, 3H), 4.51-4.75 (m, 1H), 5.87-6.20 (br, 1H) ppm

Example 5

Synthesis of (R)—N-Propylnorvalinol

Lithium aluminum hydride (5.47 g) was added to tetrahydrofuran (144 mL) with stirring at 4° C. and then stirred under ice-cooling for 15 minutes. A solution of (R)—N-propionylnorvaline methyl ester (15.87 g) in tetrahydrofuran (85 mL) was added dropwise to the resulting suspension over 70 minutes under stirring at 4° C. and then stirred for 15 minutes under ice-cooling. The suspension was refluxed and stirred for 2 hours and then stirred under ice-cooling for 20 minutes, and an aqueous solution (25 mL) of 1 mol/L sodium hydroxide was added dropwise thereto over 12 minutes and stirred under ice-cooling for 5 minutes. The suspension was refluxed and stirred for 1 hour. The suspension was filtered and washed with ethyl acetate (23 mL). The insoluble matter was subsequently washed twice with hot ethyl acetate (115 mL). The filtrate and the washings were combined and dried over anhydrous sodium sulfate for 12 hours and then concentrated under reduced pressure to give (R)—N-propylnorvalinol (11.97 g, 97% yield) as a yellow oil.

MS (m/z) 144, 114, 86, 72

IR (KBr) 3300, 2960, 2940, 2875, 1650, 1464, 1386, 1247, 1150, 1057, 902 cm$^{-1}$

NMR (CDCl$_3$) δ 0.93 (t, 6H, J=7.4 Hz), 1.20-1.64 (m, 6H), 2.44-2.73 (m, 3H), 3.25 (dd, 1H, J=6.7, 10.4 Hz), 3.60 (dd, 1H, J=4.0, 10.4 Hz) ppm Specific rotation: $[\alpha]_D^{20}$–36.47° (CHCl$_3$, c=1.074)

Example 6

Synthesis of (S)—N-Propylnorvalinol (S)—N-Propylnorvalinol (15.5 g, 96% yield) was obtained as a colorless oil, following the procedure of Example 5, but using (S)—N-propionylnorvaline methyl ester (20.7 g) and lithium aluminum hydride (8.37 g).

NMR (CDCl$_3$) δ 0.93 (t, 6H, J=7.0 Hz), 1.23-1.68 (m, 6H), 2.46-2.76 (m, 3H), 3.28 (dd, 1H, J=6.3, 10.4 Hz), 3.60 (dd, 1H, J=4.0, 10.7 Hz) ppm

Example 7

Synthesis of (R)-3,4-dipropyl-1,2,3-oxathiazolidine 2-oxide (R)—N-Propylnorvalinol (11.53 g) was dissolved in dichloromethane (160 mL), and N-methylmorpholine (21.8 mL) was added thereto under stirring at room temperature. A solution of thionyl chloride (6.9 mL) in dichloromethane (48 mL) was added dropwise to the resulting solution over 120 minutes under stirring at 2° C. The resulting suspension was stirred at room temperature for 4 hours. Water (104 mL) was added to the suspension under stirring at 3° C. The mixture was separated and the organic layer was washed with an aqueous 1 mol/L hydrochloric acid solution (104 mL) and subsequently with a saturated aqueous sodium hydrogen carbonate solution (104 mL), dried over anhydrous magnesium sulfate and then concentrated under reduced pressure. The residue was dried under reduced pressure at room temperature for 19 hours to give (R)-3,4-dipropyl-1,2,3-oxathiazolidine 2-oxide as a red oil (12.36 g, 81% yield, cis:trans=about 45:55 determined from the integration ratio in $^1$H-NMR).

MS (m/z) 190, 148, 126, 114, 98, 84

IR (KBr) 2970, 2940, 2880, 1467, 1383, 1160, 1010, 954, 915, 840, 695 cm$^{-1}$

NMR (CDCl$_3$) δ 0.97 (t, 3H, J=7.4 Hz), 1.25-1.92 (m, 6H), 2.80-3.20 (m, 2H), 3.34-3.46 (m, 0.45H, cis), 3.56-3.68 (m, 0.55H, trans), 4.02 (dd, 0.55H, J=7.7, 8.1 Hz, trans), 4.52 (d, 0.90H, J=7.1 Hz, cis), 4.78 (dd, 0.55H, J=7.1, 8.1 Hz, trans) ppm (The number of protons for the signal of each of the cis and trans forms is expressed such that the total number for the cis and trans forms becomes 1.)

Specific rotation: $[\alpha]_D^{20}$–89.00° (CHCl$_3$, c=1.208)

Example 8

Synthesis of (S)-3,4-dipropyl-1,2,3-oxathiazolidine 2-oxide

N-Methylmorpholine (27.3 mL) was added to a solution of (S)—N-propylnorvalinol (11.5 g) in dichloromethane (200 mL) under stirring at room temperature. A solution of thionyl chloride (9.32 mL) in dichloromethane (64 mL) was added dropwise to the resulting light yellow solution under ice-cooling and stirring. The resulting suspension was stirred at room temperature. Water was added to the suspension under ice-cooling and stirring, and the mixture was extracted with dichloromethane. The organic layer was washed with an aqueous 1 mol/L hydrochloric acid solution and subsequently with a saturated aqueous sodium hydrogen carbonate solution, dried over anhydrous magnesium sulfate, and then the solvent was removed by distillation under reduced pressure. The residue was dried under reduced pressure at room temperature overnight to give (S)-3,4-dipropyl-1,2,3-oxathiazolidine 2-oxide as a colorless oil (16.1 g, 79% yield, cis:trans=about 38:62 determined from the integration ratio in $^1$H-NMR).

NMR (CDCl$_3$) δ 0.85-1.10 (m, 6H), 1.25-1.85 (m, 6H), 2.80-3.19 (m, 2H), 3.36-3.44 (m, 0.38H, cis), 3.55-3.66 (m, 0.62H, trans), 4.03 (dd, 0.62H, J=7.4, 8.1 Hz, trans), 4.52 (d, 0.76H, J=7.4 Hz, cis), 4.76 (dd, 0.62H, J=7.1, 8.1 Hz, trans) ppm (The number of protons for the signal of each of the cis and trans forms is expressed such that the total number for the cis and trans forms becomes 1.)

Example 9

Synthesis of (R)-3,4-dipropyl-1,2,3-oxathiazolidine 2,2-dioxide

Ruthenium trichloride hydrate (10 mg) was added to a solution of (R)-3,4-dipropyl-1,2,3-oxathiazolidine 2-oxide (11.09 g) in ethyl acetate (58 mL) under stirring at 3° C. A cold saturated aqueous sodium periodate solution (200 mL) was added to the solution. The resulting suspension was stirred under ice-cooling for 10 minutes and then further stirred at room temperature for 1 hour. The suspension was filtered, and the insoluble matter was washed twice with ethyl acetate (15 mL). The filtrate and the washings were combined. The organic layer was separated, washed with a saturated aqueous sodium hydrogen carbonate solution (15 mL), dried over anhydrous sodium sulfate and then concentrated under reduced pressure. Tetrahydrofuran (13.5 mL) was added to the residue, and the mixture was concentrated under reduced pressure. The concentration was repeated three times. (R)-3,4-Dipropyl-1,2,3-oxathiazolidine 2,2-dioxide (11.22 g, 93% yield) was obtained as a brown oil.

MS (m/z) 206, 178, 164, 136, 122, 112, 94, 85, 70, 69

IR (KBr) 2980, 2950, 2890, 1472, 1347, 1271, 1186, 1115, 1056, 974, 920, 895, 813, 720, 662 cm$^{-1}$

NMR (CDCl$_3$) δ 0.98 (t, 3H, J=7.4 Hz), 0.98 (t, 3H, J=7.4 Hz), 1.24-1.44 (m, 2H), 1.50-1.85 (m, 4H), 2.88-3.10 (m, 1H), 3.12-3.24 (m, 1H), 3.53-3.65 (m, 1H), 4.17 (dd, 1H, J=7.1, 8.4 Hz), 4.54 (dd, 1H, J=6.4, 8.4 Hz) ppm Specific rotation: [α]$_D^{20}$−57.65° (CHCl$_3$, c=1.284)

Example 10

Synthesis of (S)-3,4-dipropyl-1,2,3-oxathiazolidine 2,2-dioxide (S)-3,4-Dipropyl-1,2,3-oxathiazolidine 2,2-dioxide (17.0 g, 98% yield) was obtained as a colorless oil, following the procedure of Example 9, but using (S)-3,4-dipropyl-1,2,3-oxathiazolidine 2-oxide (16.1 g), ruthenium trichloride hydrate (20 mg) and sodium periodate (21.5 g).

MS (m/z) 207, 178, 164, 136, 122, 85, 69

IR (KBr) 2966, 2937, 2877, 1468, 1342, 1267, 1186, 1113, 1011, 972, 810, 719, 629 cm$^{-1}$

NMR (CDCl$_3$) δ 0.98 (t, 3H, J=7.4 Hz), 0.98 (t, 3H, J=7.1 Hz), 1.23-1.43 (m, 2H), 1.50-1.88 (m, 4H), 2.88-3.00 (m, 1H), 3.12-3.23 (m, 1H), 3.54-3.65 (m, 1H), 4.17 (dd, 1H, J=7.1, 8.4 Hz), 4.54 (dd, 1H, J=6.7, 8.4 Hz) ppm Specific rotation: [α]$_D^{20}$+58.28° (CHCl$_3$, c=1.098)

Example 11

Synthesis of (S)-3,4-dipropyl-1,2,3-oxathiazolidine 2,2-dioxide

Ruthenium dioxide hydrate (3 mg) and a phosphate buffer solution (pH 7.4, 28.7 mL) were subsequently added to a solution of (S)-3,4-dipropyl-1,2,3-oxathiazolidine 2-oxide (5.74 g) in ethyl acetate (46 mL) under ice-cooling and stirring. Sodium periodate (7.06 g) was added to the solution under ice-cooling and stirring, and then vigorously stirred at room temperature for 30 minutes. The suspension was filtered, and the insoluble matter was washed with ethyl acetate (17 mL). The filtrate and the washings were combined. The organic layer was separated and washed subsequently with a saturated aqueous sodium hydrogen carbonate solution (11.5 mL), an aqueous 10% sodium thiosulfate solution (11.5 mL) and a saturated aqueous sodium chloride solution (11.5 mL). Anhydrous sodium sulfate and activated carbon (0.57 g) were added to the organic layer and stirred at room temperature for 1 hour. The suspension was filtered, and the filtrate was concentrated under reduced pressure. The residue was added with tetrahydrofuran (8.6 mL) and concentrated under reduced pressure at 40° C. or lower to give (S)-3,4-dipropyl-1,2,3-oxathiazolidine 2,2-dioxide (5.83 g, 94% yield) as an orange-brown oil.

Example 12

Synthesis of (R)-1-(benzofuran-2-yl)-2-propylaminopentane Hydrochloride

Under an argon atmosphere, n-butyl lithium (a 1.57 mol/L hexane solution, 14.3 mL) was added dropwise over 10 minutes to a solution of benzofuran (2.47 mL) in tetrahydrofuran (14.3 mL) under stirring at 2° C. Under stirring at 2° C., 1,2-dimethoxyethane (2.33 mL) was added to the resulting solution and stirred at 2° C. for 30 minutes. Under stirring at 2° C., a solution of (R)-3,4-dipropyl-1,2,3-oxathiazolidine 2,2-dioxide (4.22 g) in tetrahydrofuran (10.2 mL) was added dropwise to the resulting solution over 5 minutes and stirred at 2° C. for 1 hour. Water (10.2 mL) was added to the solution under stirring at 3° C. The solution was stirred under ice-cooling for 15 minutes and then an aqueous layer was separated. The organic layer was extracted with water (10.2 mL) again. The aqueous layers were combined and washed with toluene (10.2 mL). An aqueous 10 mol/L hydrochloric acid solution (8.2 mL) was added to the aqueous layer under stirring at 2° C. The resulting suspension was stirred under ice-cooling for 5 minutes and then stirred at room temperature for 2 hours. After the suspension was stirred at 2° C. for 1 hour, the precipitated crystals were collected by filtration. The resulting crystals were suspended in diisopropyl ether (20.4 mL) and vigorously stirred at room temperature for 30 minutes. The crystals were separated by filtration and washed with diisopropyl ether (10.2 mL). The crystals were suspended in diisopropyl ether (40.8 mL), and under stirring at room temperature, a 1 mol/L sodium hydroxide solution (25 mL) was added thereto. The resulting two-layer solution was vigorously stirred at room temperature for about 1 hour so that the crystals were dissolved. The two-layer solution was allowed to separate. The organic layer was dried over anhydrous sodium sulfate and then filtered, and the sodium sulfate was washed twice with diisopropyl ether (5.1 mL). Saturated hydrogen chloride in diethyl ether (10.2 mL) was added to the solution under stirring at 2° C. and then stirred under ice-cooling for 15 minutes. The precipitated crystals were collected by filtration and washed twice with diisopropyl ether (20.4 mL). The crystal (4.40 g) was suspended in 2-propanol (44 mL) and dissolved by refluxing and stirring. The solution was allowed to stand at room temperature for 17 hours. The precipitated crystals were collected by filtration and washed with cold diisopropyl ether (3° C., 11 mL twice) to give (R)-1-(benzofuran-2-yl)-2-propylaminopentane hydrochloride (2.97 g, 52% yield) as white needles.

Melting point: 165-167° C.

MS (m/z) 244, 114, 72

IR (KBr) 2950, 2850, 2775, 2710, 2675, 2505, 2440, 1600, 1465, 1448, 1377, 1318, 1248, 1200, 1172, 1120, 1105, 1080, 1022, 1003, 944, 920, 876, 831, 803, 770, 760 cm$^{-1}$

NMR (CDCl$_3$) δ 0.91 (t, 3H, J=7.4 Hz), 0.94 (t, 3H, J=7.4 Hz), 1.33-2.10 (m, 6H), 2.77-3.05 (m, 2H), 3.27 (dd, 1H, J=9.8, 16.1 Hz), 3.40-3.68 (m, 2H), 6.65 (s, 1H), 7.10-7.35 (m, 2H), 7.35-7.45 (m, 1H), 7.45-7.60 (m, 1H), 9.37-9.83 (br, 2H) ppm Elemental analysis: Calcd.: C, 68.19; H, 8.58; N, 4.97. Found: C, 68.32; H, 8.40; N, 4.87

Specific rotation: [α]$_D^{20}$−4.23° (MeOH, c=4.400)

Optical purity: 98% ee (determined by HPLC analysis with chiral column)

Example 13

Synthesis of (S)-1-(benzofuran-2-yl)-2-propylaminopentane Hydrochloride

Under an argon atmosphere, n-butyl lithium (a 1.56 mol/L hexane solution, 57.9 mL) was added to a solution of benzofuran (9.95 mL) in tetrahydrofuran (58 mL) under ice-cooling and stirring. Under ice-cooling and stirring, 1,2-dimethoxyethane (9.38 mL) was added to the resulting solution and stirred under ice-cooling for 30 minutes. Under water-cooling and stirring, a solution of (S)-3,4-dipropyl-1,2,3-oxathiazolidine 2,2-dioxide (17.0 g) in tetrahydrofuran (40 mL) was added dropwise to the resulting solution and stirred under ice-cooling for 1 hour. Water was added to the solution under ice-cooling and stirring, and then an aqueous layer was separated. The organic layer was extracted with water again. The aqueous layers were combined and washed with toluene. An aqueous 10 mol/L hydrochloric acid solution was added to the aqueous layer under ice-cooling and stirring. The resulting suspension was stirred under ice-cooling and then stirred at room temperature for 2 hours. The suspension was again stirred under ice-cooling for 1 hour, and the precipitated crystals were collected by filtration. The resulting crystals were recrystallized from acetone. (S)-1-(Benzofuran-2-yl)-2-propylaminopentane hydrochloride (10.8 g, 47% yield) was obtained as colorless needles.

Melting point: 170-171° C.

MS (m/z) 246, 202, 131, 115, 72

IR (KBr) 2980, 2890, 2800, 2750, 2710, 2525, 2440, 1602, 1588, 1478, 1460, 1383, 1353, 1320, 1256, 1256, 1178, 1140, 1120, 1108, 1080, 1048, 1023, 1007, 953, 925, 880, 835, 805, 777, 765, 720 cm$^{-1}$

NMR (CDCl$_3$) δ 0.91 (t, 3H, J=7.4 Hz), 0.94 (t, 3H, J=7.4 Hz), 1.35-2.10 (m, 6H), 2.80-3.00 (m, 2H), 3.26 (dd, 1H, J=9.4, 16.4 Hz), 3.50-3.60 (m, 2H), 6.65 (s, 1H), 7.15-7.30 (m, 2H), 7.40-7.45 (m, 1H), 7.49-7.53 (m, 1H), 9.35-9.70 (br, 2H) ppm Elemental analysis: Calcd.: C, 68.19; H, 8.58; N, 4.97. Found: C, 68.31; H, 8.44; N, 4.84

Specific rotation: $[\alpha]_D^{20}$ −4.37° (MeOH, c=4.000)

Example 14

Synthesis of (R)-1-(2-benzothienyl)-2-propylaminopentane Hydrochloride

Under an argon atmosphere, n-butyl lithium (a 1.56 mol/L hexane solution, 44.4 mL) and 1,2-dimethoxyethane (7.2 mL) were added to a solution of benzothiophene (8.45 g) in tetrahydrofuran (120 mL) under ice-cooling and stirring and then stirred under ice-cooling for 30 minutes. A solution of (R)-3,4-dipropyl-1,2,3-oxathiazolidine 2,2-dioxide (14.36 g) in tetrahydrofuran (43.0 mL) was added dropwise to the resulting solution and stirred under ice-cooling for 2.5 hours. Under ice-cooling and stirring, 1 mol/L hydrochloric acid (200 mL) was added to the resulting solution and stirred at room temperature for 1.5 hours. Diethyl ether (200 mL) was added to the solution, and the mixture was separated. The aqueous layer was neutralized with 1 mol/L sodium hydroxide and then extracted with diethyl ether. The organic layer was washed with water and a saturated aqueous sodium chloride solution, dried over anhydrous sodium sulfate and then concentrated under reduced pressure. Saturated hydrogen chloride in diethyl ether (10 mL) was added to a solution of the residue in diethyl ether (50 mL) under ice-cooling and stirring. After stirring at the same temperature for several minutes, the solvent was removed under reduced pressure. The residue was recrystallized from ethanol (100 mL) to give (R)-1-(2-benzothienyl)-2-propylaminopentane hydrochloride (13.17 g, 70% yield) as white crystals.

Melting point: 192-194° C.

MS (m/z) 262, 218, 147, 114, 72

IR (KBr) 2971, 2960, 2871, 2805, 2736, 2694, 2518, 2431, 1606, 1594, 1459, 1432, 1118, 836, 761 cm$^{-1}$

NMR (CDCl$_3$) δ 0.91 (t, 3H, J=7.4 Hz), 0.97 (t, 3H, J=7.4 Hz), 1.40-2.15 (m, 6H), 2.80-3.05 (br, 2H), 3.30-3.50 (m, 2H), 3.65-3.85 (m, 1H), 7.22 (s, 1H), 7.25-7.40 (m, 2H), 7.65-7.85 (m, 2H), 9.45-9.85 (br, 2H) ppm Elemental analysis: Calcd.: C, 64.51; H, 8.12; N, 4.70. Found: C, 64.44; H, 7.98; N, 4.52.

Specific rotation: $[\alpha]_D^{20}$ −18.60° (CHCl$_3$, c=1.012)

Example 15

Synthesis of (R)-1-(3,4-methylenedioxyphenyl)-2-propylaminopentane

Under an argon atmosphere, 1,2-dimethoxyethane (7.1 mL) was added to a solution of 4-bromo-1,2-methylenedioxybenzene (8.2 mL) in tetrahydrofuran (140 mL) under stirring at room temperature. Under stirring at −72° C., n-butyl lithium (a 1.57 mol/L hexane solution, 86.9 mL) was added dropwise to the resulting solution over 30 minutes. The resulting suspension was stirred at −50° C. or lower for 1 hour. Under stirring at −45° C., a solution of (R)-3,4-dipropyl-1,2,3-oxathiazolidine 2,2-dioxide (14.14 g) in tetrahydrofuran (34 mL) was added dropwise to the suspension over 20 minutes. The solution was stirred at 10° C. or lower for 2 hours. Water (200 mL) was added to the solution under stirring at room temperature, and the mixture was separated. To the aqueous layer was added concentrated hydrochloric acid (22.8 mL) and then diethyl ether (70 mL) under stirring at room temperature. After vigorous stirring at room temperature for 2 hours, the resulting two-layer solution was separated, and the ether layer was extracted with an aqueous 1 mol/L hydrochloric acid solution (200 mL). The aqueous layer was made basic with an aqueous 1 mol/L sodium hydroxide solution, and the organic layer and diethyl ether (100 mL) were added thereto. The organic layer was separated, washed with a saturated aqueous sodium chloride solution (30 mL), dried over anhydrous magnesium sulfate and then concentrated under reduced pressure. The residue was purified by column chromatography (NH-DM1020, AcOEt/Hexane=1/9) to give (R)-1-(3,4-methylenedioxyphenyl)-2-propylaminopentane (8.00 g, 47% yield) as a yellow oil.

NMR (CDCl$_3$) δ 0.85 (t, 3H, J=7.7 Hz), 0.76-1.02 (m, 3H), 1.25-1.55 (m, 6H), 2.43-2.75 (m, 5H), 5.92 (s, 2H), 6.60-6.80 (m, 3H) ppm Example 16

Synthesis of (R)-1-(3,4-methylenedioxyphenyl)-2-propylaminopentane Hydrochloride Saturated hydrogen chloride in diethyl ether (15 mL) was added to a solution of (R)-1-(3,4-methylenedioxyphenyl)-2-propylaminopentane (8.00 g) in diethyl ether (80 mL) under ice-cooling and stirring. The precipitated crystals were collected by filtration and washed four times with diethyl ether (1 mL). The resulting powder (7.44 g) was dissolved by heating in acetone (150 mL), and the solution was concentrated to about 100 mL. The solution was allowed to stand at 5° C. for 15 hours. The precipitated crystals were collected by filtration and washed three times with acetone (5 mL) to give (R)-1-(3,4-methylenedioxyphenyl)-2-propylaminopentane hydrochloride (4.58 g, 24% yield).

Melting point: 174-176° C.

MS (m/z) 250, 206, 135, 114, 72

IR (KBr) 2996, 2875, 2800, 2746, 2526, 2438, 1608, 1595, 1506, 1491, 1450, 1367, 1248, 1192, 1126, 1105, 1036, 991, 930, 874, 810, 779, 758, 739, 715, 642, 611, 569, 503, 422 cm$^{-1}$

NMR (CDCl$_3$) δ 0.87 (t, 3H, J=7.4 Hz), 0.97 (t, 3H, J=7.4 Hz), 1.30-1.87 (m, 4H), 1.88-2.09 (m, 2H), 2.89 (dd, 1H,

J=9.1, 13.5 Hz), 3.17-3.33 (m, 1H), 3.37 (dd, 1H, J=5.0, 13.5 Hz), 5.95 (s, 2H), 6.74 (s, 3H), 7.25-7.40 (m, 2H), 9.30-9.75 (br, 2H) ppm Elemental analysis: Calcd.: C, 63.04; H, 8.46; N, 4.90. Found: C, 62.74; H, 8.23; N, 4.82.

Specific rotation: $[\alpha]_D^{20}$ –4.99° (MeOH, c=1.014)

Example 17

Synthesis of (R)-1-(1-triisopropylsilylindole-3-yl)-2-propylaminopentane

Under an argon atmosphere, s-butyl lithium (a 0.99 mol/L cyclohexane/n-hexane solution, 68.7 mL) was added to a solution of 2-bromo-1-triisopropylsilylindole (11.99 g) in tetrahydrofuran (85 mL) under stirring at –70° C. and then stirred at –70° C. for 30 minutes. A solution of (R)-3,4-dipropyl-1,2,3-oxathiazolidine 2,2-dioxide (7.05 g) in tetrahydrofuran (17 mL) was added to the resulting solution under stirring at –20° C. and then stirred for 13 hours, while the temperature was raised to room temperature. An aqueous 4 mol/L hydrochloric acid solution (34 mL) was added to the solution under water-cooling and stirring, and then vigorously stirred at room temperature for 1 hour. The organic layer was separated, washed with a saturated aqueous sodium hydrogen carbonate solution (30 mL), dried over anhydrous sodium sulfate and then concentrated under reduced pressure. The residue was subjected to column chromatography (NH-DM1020, from Hexane to AcOEt/Hexane=1/7) and then further purified by column chromatography (NH-DM1020, from AcOEt/Hexane=1/9 to AcOEt/MeOH=9/1) to give (R)-1-(1-triisopropylsilylindole-3-yl)-2-propylaminopentane (9.94 g, 73% yield) as a red oil.

MS (m/z) 400, 287, 244, 114

IR (neat) 2954, 2870, 1608, 1558, 1464, 1450, 1381, 1313, 1213, 1163, 1140, 1074, 1016, 995, 962, 922, 883, 758, 739, 688, 658, 567, 519 cm$^{-1}$ NMR (CDCl$_3$) δ 0.77 (t, 3H, J=7.4 Hz), 0.93 (t, 3H, J=6.7 Hz), 1.17 (d, 18H, J=7.4 Hz), 1.18-1.58 (m, 6H), 1.69 (qq, 3H, J=7.4, 7.4 Hz), 2.35-2.49 (m, 1H), 2.55-2.68 (m, 1H), 2.73 (dd, 1H, J=7.7, 13.1 Hz), 2.70-2.90 (m, 1H), 2.93 (dd, 1H, J=4.0, 13.1 Hz), 7.07 (s, 1H), 7.09-7.19 (m, 2H), 7.44-7.53 (m, 1H), 7.55-7.63 (m, 1H) ppm Example 18

Synthesis of (R)-1-(3-indolyl)-2-propylaminopentane

Tetra-n-butylammonium fluoride (9.64 g) was added to a solution of (R)-1-(1-triisopropylsilylindole-3-yl)-2-propylaminopentane (9.85 g) in tetrahydrofuran (45 mL) under stirring at room temperature and then stirred at room temperature for 50 minutes. A saturated aqueous sodium hydrogen carbonate solution (20 mL) and diethyl ether (40 mL) were added to the resulting solution. The organic layer was separated, washed with a saturated aqueous sodium hydrogen carbonate solution, dried over anhydrous sodium sulfate and then concentrated under reduced pressure. The residue was subjected to column chromatography (NH-DM1020, AcOEt/Hexane=1/6). An aqueous 1 mol/L hydrochloric acid solution (100 mL) and diethyl ether (100 mL) were added to the resulting oil, and then the organic layer was extracted with an aqueous 1 mol/L hydrochloric acid solution. The aqueous layers were combined and washed with diethyl ether (30 mL). The aqueous layer was made basic with an aqueous 1 mol/L sodium hydroxide solution and extracted twice with diethyl ether (60 mL). The organic layers were combined and washed with a saturated aqueous sodium hydrogen carbonate solution, dried over anhydrous sodium sulfate and then concentrated under reduced pressure to give (R)-1-(3-indolyl)-2-propylaminopentane (5.78 g, 96% yield) as a light orange oil.

NMR (CDCl$_3$) δ 0.81 (t, 3H, J=7.4 Hz), 0.93 (t, 3H, J=6.7 Hz), 1.25-1.65 (m, 6H), 2.44-2.57 (m, 1H), 2.57-2.70 (m, 1H), 2.71-2.98 (m, 3H), 7.02 (d, 1H, J=2.4 Hz), 7.11 (ddd, 1H, J=1.0, 7.7, 8.1 Hz), 7.19 (ddd, 1H, J=1.0, 7.7, 8.1 Hz), 7.36 (dd, 1H, J=1.0, 8.1 Hz), 7.62 (d, 1H, J=7.7 Hz) ppm Example 19

Synthesis of (R)-1-(3-indolyl)-2-propylaminopentane hydrochloride

Saturated hydrogen chloride in diethyl ether (20 mL) was added to a solution of (R)-1-(3-indolyl)-2-propylaminopentane (7.13 g) in diethyl ether under ice-cooling and stirring and then stirred at the same temperature for 10 minutes. The precipitated crystals were collected by filtration and washed three times with diethyl ether (10 mL). The resulting powder (7.70 g) was suspended in acetone (20 mL), and the suspension was stirred and refluxed for 10 minutes. The resulting yellow suspension was filtered, and the crystals were washed with acetone (5 mL three times) to give (R)-1-(3-indolyl)-2-propylaminopentane hydrochloride (4.43 g, 53% yield).

Melting point: 177-178° C.

MS (m/z) 245, 244, 130, 114, 72

IR (KBr) 3238, 2956, 2800, 2744, 2571, 2511, 2420, 1620, 1593, 1552, 1493, 1458, 1431, 1381, 1356, 1338, 1234, 1097, 1066, 1011, 980, 931, 876, 802, 748, 683, 625, 588, 565, 459, 428 cm$^{-1}$

NMR (CDCl$_3$) δ 0.82 (t, 3H, J=7.4 Hz), 0.88 (t, 3H, J=7.4 Hz), 1.40-1.70 (m, 2H), 1.70-2.02 (m, 4H), 2.65-2.97 (m, 2H), 3.10-3.32 (m, 1H), 3.32-3.52 (m, 2H), 7.10 (ddd, 1H, J=1.0, 7.1, 7.7 Hz), 7.119 (ddd, 1H, J=1.0, 7.1, 8.1 Hz), 7.27 (d, 1H, J=2.4 Hz), 7.39 (dd, 1H, J=1.0, 8.1 Hz), 7.60 (d, 1H, J=7.7 Hz), 8.64 (s, 1H), 9.00 (br, 1H), 9.44 (br, 1H) ppm Elemental analysis: Calcd.: C, 68.43; H, 8.97; N, 9.98. Found: C, 68.45; H, 8.80; N, 9.90.

Specific rotation: $[\alpha]_D^{20}$ –14.91° (MeOH, c=1.004)

The invention claimed is:

1. A process for preparing an optically active aminopentane derivative represented by formula (8):

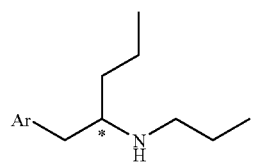

(8)

wherein Ar represents phenyl, thienyl, naphthyl, benzofuryl, benzothienyl, methylenedioxyphenyl or indolyl which may have a substitution of C1 to C3 alkyl group, and * indicates the position of an asymmetric carbon atom in the R or S configuration, said process comprising the steps of:

i) treating an optically active oxathiazolidine derivative represented by formula (5-2):

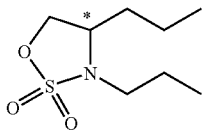
(5-2)

wherein * indicates the position of an asymmetric carbon atom in the R or S configuration, to react with an aryl lithium represented by formula (6):

Ar—Li    (6)

wherein Ar has the same meaning as defined above, to obtain an optically active lithium N-sulfonate derivative represented by formula (7):

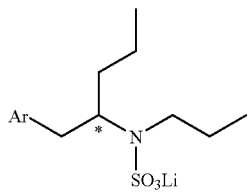
(7)

wherein Ar and * each has the same meaning as defined above, and ii) hydrolyzing the optically active lithium N-sulfonate derivative represented by formula (7) to hydrolyze with an acid.

2. The process according to claim 1, wherein the optically active oxathiazolidine derivative represented by formula (5-2) is obtained by treating an optically active oxathiazolidine derivative represented by formula (5-1):

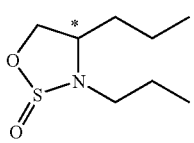
(5-1)

wherein * has the same meaning as defined above,
with an oxidizing agent in the presence of a ruthenium catalyst.

3. The process according to claim 2, wherein the compound represented by formula (5-1) is obtained by a process comprising the steps of:

i) esterifying an optically active norvaline represented by formula (1):

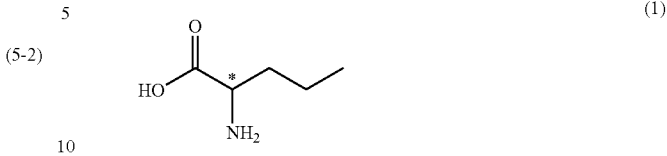
(1)

wherein * has the same meaning as defined above,
with an alcohol pretreated with thionyl chloride to obtain an optically active norvaline ester derivative represented by formula (2):

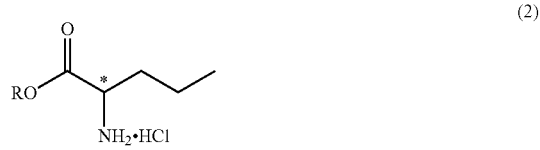
(2)

wherein R represents a C1 to C6 alkyl group, and * has the same meaning as defined above;

ii) treating the optically active norvaline ester derivative of formula (2) with propionic anhydride in the presence of a base to obtain an optically active N-propionylnorvaline ester derivative represented by formula (3):

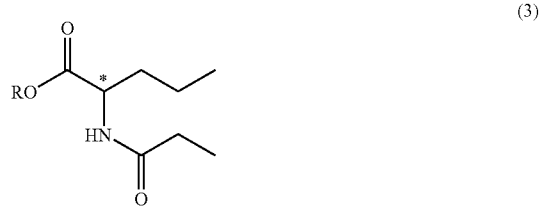
(3)

wherein R and * each has the same meaning as defined above;

iii) treating the optically active N-propionylnorvaline ester derivative of formula (3) with a reducing agent to obtain an optically active N-propylnorvalinol represented by formula (4):

(4)

wherein * has the same meaning as defined above; and iv) treating the optically active N-propylnorvalinol of formula (4) with thionyl chloride in the presence of a base.

4. The process according to any one of claims 1 to 3, wherein the aryl group represented by Ar in formulae (6) to (8) is 2-benzofuryl or benzothienyl.

* * * * *